United States Patent
Tanaka et al.

(10) Patent No.: US 9,121,821 B2
(45) Date of Patent: Sep. 1, 2015

(54) PROCESS FOR ANALYZING SAMPLE BY CAPILLARY ELECTROPHORESIS METHOD

(75) Inventors: Yoshihide Tanaka, Osaka (JP); Shinichi Wakida, Osaka (JP); Yusuke Nakayama, Kyoto (JP); Satoshi Yonehara, Kyoto (JP)

(73) Assignees: National Institute of Advanced Industrial Science and Technology, Tokyo (JP); ARKRAY, Inc., Kyoto (JP)

( * ) Notice: Subject to any disclaimer, the term of this patent is extended or adjusted under 35 U.S.C. 154(b) by 642 days.

(21) Appl. No.: 12/376,739

(22) PCT Filed: Aug. 29, 2007

(86) PCT No.: PCT/JP2007/066751
§ 371 (c)(1),
(2), (4) Date: Mar. 20, 2009

(87) PCT Pub. No.: WO2008/029684
PCT Pub. Date: Mar. 13, 2008

(65) Prior Publication Data
US 2010/0175996 A1    Jul. 15, 2010

(30) Foreign Application Priority Data

Sep. 4, 2006   (JP) .................................. 2006-239640

(51) Int. Cl.
*G01N 27/447* (2006.01)
(52) U.S. Cl.
CPC ........ *G01N 27/447* (2013.01); *G01N 27/44756* (2013.01)
(58) Field of Classification Search
CPC ..................... G01N 27/447; B01L 2400/0415; B01L 2400/0421; B01L 3/502; C07K 1/28; B01D 57/02

USPC .......... 204/450–470, 600–621, 622, 641–645
See application file for complete search history.

(56) References Cited

U.S. PATENT DOCUMENTS 5,192,406 A * 3/1993 Woolley ........................ 204/454
5,292,416 A   3/1994 Novotny et al. ........... 204/182.8
(Continued)

FOREIGN PATENT DOCUMENTS

EP        0708329 A1    4/1996
JP        4-320957      11/1992
(Continued)

OTHER PUBLICATIONS

Y. Du, S. Honda, A. Taga, W. Liu, S. Suzuki, A novel Polybrene/Chondroitin Sulfate C Double Coated Capillary and Its Application in Capilarry Electrophoresis, Chinese Journal of Chemistry, (2002), 20, 1557-1565.*

(Continued)

*Primary Examiner* — Luan Van
*Assistant Examiner* — Maris R Kessel
(74) *Attorney, Agent, or Firm* — Morgan, Lewis & Bockius LLP (57) ABSTRACT

A process for analyzing a sample by a capillary electrophoresis method is provided that allows for high analytic precision and reduction in apparatus size, and can be readily carried out by electrophoresing a complex of a sample and an anionic group-containing compound in the capillary channel, wherein the capillary channel includes an A layer that is coated on an inner wall thereof and a B layer that is coated on the A layer, where the A and B layers are as described.

11 Claims, 9 Drawing Sheets

Example 1

(56) References Cited

U.S. PATENT DOCUMENTS

| | | | |
|---|---|---|---|
| 5,314,593 A | 5/1994 | Swedberg | |
| 5,431,793 A | 7/1995 | Wang et al. | |
| 5,599,433 A * | 2/1997 | Keo et al. | 204/451 |
| 5,611,903 A * | 3/1997 | Janssens et al. | 204/454 |
| 6,107,038 A * | 8/2000 | Choudhary et al. | 435/6.12 |
| 6,428,704 B1 | 8/2002 | Setoguchi et al. | |
| 6,586,065 B1 | 7/2003 | Katayama et al. | 428/36.9 |
| 2004/0256232 A1 | 12/2004 | Jiang et al. | |
| 2005/0025675 A1 | 2/2005 | Schlenoff et al. | |
| 2005/0163853 A1 | 7/2005 | Szente et al. | 424/486 |
| 2005/0274616 A1 | 12/2005 | Frederic et al. | 204/451 |
| 2006/0040396 A1 | 2/2006 | Baba et al. | |
| 2006/0102478 A1 | 5/2006 | Robert et al. | |
| 2006/0113189 A1 | 6/2006 | Hiratsuka et al. | |
| 2007/0017870 A1 | 1/2007 | Belov et al. | 210/656 |
| 2010/0101953 A1 | 4/2010 | Yokoyama et al. | 204/601 |

FOREIGN PATENT DOCUMENTS

| | | | |
|---|---|---|---|
| JP | 5-503989 | 6/1993 | |
| JP | 6-288984 | 10/1994 | |
| JP | 8-094578 | 4/1996 | |
| JP | 8-504037 | 4/1996 | |
| JP | 9-105739 | 4/1997 | |
| JP | H09-143202 | 6/1997 | C08B 37/00 |
| JP | 9-510792 | 10/1997 | |
| JP | H10-502175 | 2/1998 | G01N 27/447 |
| JP | 10-505166 | 5/1998 | |
| JP | H10-221305 | 8/1998 | G01N 27/447 |
| JP | 2002-350413 | 12/2002 | G01N 30/48 |
| JP | 3429709 B2 | 5/2003 | |
| JP | 2004-286449 | 10/2004 | G01N 27/447 |
| JP | 2005-249572 | 9/2005 | G01N 27/447 |
| JP | 2005-291926 | 10/2005 | |
| JP | 2005-326407 | 11/2005 | G01N 24/447 |
| JP | 2006-016313 | 1/2006 | A61K 31/726 |
| JP | 2006-145537 | 6/2006 | |
| JP | 2008-170351 | 7/2008 | |
| JP | 2008-164382 | 7/2009 | |
| JP | 2008-170350 | 7/2009 | |
| WO | 91/06851 A1 | 5/1991 | |
| WO | 95/09360 A1 | 4/1995 | |
| WO | 96/22524 A1 | 7/1996 | |
| WO | 96/23221 A1 | 8/1996 | |
| WO | WO 96/23220 | 8/1996 | |
| WO | WO 2004/031757 | 4/2004 | |
| WO | WO 2008/078781 | 7/2008 | |

OTHER PUBLICATIONS

Timothy W. Graul and Joseph B. Schlenoff, Capillaries Modified by Polyelectrolyte Multilayers for Electrophoretic Separations, Anal. Chem., 71, 4007-4013.*

Q. Liu, F. Lin, R. A. Hartwick, Poly(diallyldimethylammonium chloride) as a cationic coating for capillary electrophoresis, Journal of Chromatographic Science, vol. 35, No. 3, 126-130 (Mar. 1997).*

C. Yang, Z. E. Rassi, Capillary Zone Electrophoresis of proteins with fused-silica capillaries having polymers and surfactants adsorbed onto surfactant moieties previously covalently bound to the capillary column surface, Electrophoresis 19, 2278-2284, 1998.*

Kamiya, Masato et al. "Preparation of Ionic Polymer Coated Capillaries for Electrophoretic Analysis. 2", The Abstract of the 25th Symposium on Capillary Electrophoresis, The Division of Electrophoresis of the Japan Society for Analytical Chemistry, pp. 13-14, Nov. 15, 2005.

Doelman, Cees J.A. et al., "Capillary Electrophoresis System for Hemoglobin $A_{1c}$ Determinations Evaluated", Clinical Chemistry Vo. 43, No. 4, pp. 644-648, 1997.

Sirén, Heli et al., "Direct Monitoring of Glycohemoglobin $A_{1c}$ in the Blood Samples of Diabetic Patients by Capillary Electrophoresis Comparison with an Immunoassay Method", Journal of Chromatography A, vol. 979, pp. 201-207, 2002.

Office Action issued in a related U.S. Appl. No. 12/367,260, dated Sep. 15, 2011.

Office Action of related Chinese Patent Application No. 200780029543.4 issued dated Aug. 30, 2011 (English language translation included).

Office Action issued in a related U.S. Appl. No. 12/367,260, dated Jan. 9, 2012.

Office Action issued Oct. 21, 2011 in corresponding Chinese Patent Application No. 200780029192.7 (English language translation included).

Office Action issued in related U.S. Appl. No. 12/367,260 dated Aug. 6, 2012.

Office Action issued in related U.S. Appl. No. 12/635,472 dated Jul. 7, 2014.

Office Action issued in technologically related U.S. Appl. No. 12/635,472 dated Sep. 18, 2012.

Office Action issued in technically related U.S. Appl. No. 12/367,260 dated Feb. 15, 2013.

Office Action issued in technically related U.S. Appl. No. 12/367,260 dated Dec. 18, 2013.

Viklund et al., "Chromatographic Interactions between Proteins and Sulfoalkylbetaine-Based Zwitterionic Copolymers in Fully Aqueous Low-Salt Buffers," Analytical Chemistry, 73: 444-452 (2001).

Office Action issued in technically related U.S. Appl. No. 12/635,472 dated Jan. 10, 2014.

Extended European Search Report issued for corresponding European Patent Application No. 07806228.8 dated Mar. 23, 2012.

Horvath et al., "Polymer wall coatings for capillary electrophoresis," Electrophoresis, 22: 644-655 (2001).

Liu et al., "Dynamic Coating Using Polyelectrolyte Multilayers for Chemical Control of Electroosmotic Flow in Capillary Electrophoresis Microchips," Anal. Chem., 72: 5939-5944 (2000).

Yu et al., "Online concentration and separation of basic proteins using a cationic polyelectrolyte in the presence of reversed electroosmotic flow," Electrophoresis, 27: 3569-3577 (2006).

Office Action issued in related U.S. Appl. No. 12/635,472 dated Apr. 24, 2012.

Extended European Search Report issued for related European Patent Application No. 07806229.6 dated Mar. 23, 2012.

Doherty et al., "Microchannel wall coatings for protein separations by capillary and chip electrophoresis," Electrophoresis, 24: 34-54 (2003).

Dolnik, "Wall coating for capillary electrophoresis on microchips," Electrophoresis, 25: 3589-3601 (2004).

Kodama et al., "A sulfonated capillary that gives reproducible migration times for capillary zone electrophoresis and micellar electrokinetic chromatography," Electrophoresis, 26: 4070-4078 (2005).

* cited by examiner

PROCESS FOR ANALYZING SAMPLE BY CAPILLARY ELECTROPHORESIS METHOD

The present application is a U.S. National Phase Application of International Application No. PCT/JP2007/066751, filed Aug. 29, 2007, which claims the benefit of Japanese Patent Application No. 2006-239640, filed Sep. 4, 2006, both of which are hereby incorporated by reference in their entirety.

TECHNICAL FIELD

The present invention relates to a process for analyzing a sample by a capillary electrophoresis method as well as a capillary channel and a capillary electrophoresis apparatus that are used for the process.

BACKGROUND ART

In the capillary electrophoresis method, ions that have gathered on the inner wall of a capillary channel are transferred upon voltage application to generate an electroosmotic flow, which transfers the sample, and thus electrophoresis is performed. For the capillary channel, one made of fused silica is used. In this case, however, adsorption of the sample may prevent a good electroosmotic flow from being obtained. Accordingly, techniques of coating the inner walls of capillary channels have been proposed (Patent Documents 1, 2, 3, and 4). On the other hand, hemoglobin (Hb) in blood reacts with glucose in the blood to become glycated Hb. The glycated Hb in the blood reflects the past history of the blood glucose level in a biological body and therefore is considered as an index in, for example, diagnosis and treatment of diabetes. Particularly, glycated beta chain N-terminal valine is called hemoglobin A1c (HbA1c) and is measured by for example, a laboratory test, as an especially important index. Examples of the method of measuring hemoglobin in blood include an agarose electrophoresis method, a capillary electrophoresis method, an HPLC method, an immunization method, an enzymatic method, etc. Among these, those allowing minute variations such as hemoglobin variants to be detected are the capillary electrophoresis method and the HPLC method. On the other hand, an apparatus for analyzing hemoglobin is required to be reduced in size. With respect to this point, it is difficult to reduce the size of the whole apparatus in the HPLC method. On the other hand, the capillary electrophoresis method allows the size of the whole apparatus to be reduced, with the apparatus being formed into a microchip.

However, there is a problem in that the aforementioned conventional capillary electrophoresis method does not allow hemoglobin to be analyzed with high precision. In order to solve this problem, there is a technique in which the inner wall of a capillary channel is coated with a protein, which then is coated with polysaccharide (Patent Document 5). However, in this technique, an operation is required in which the inner wall of a capillary channel is coated with a protein each time the analysis is carried out, and therefore there is a problem in that the analysis becomes complicated. On the other hand, there is a method in which capillary electrophoresis is carried out with a zwitterionic type of running buffer that is allowed to contain a flow inhibitor such as aliphatic diamine, with the inner wall of the capillary channel not being coated (Patent Document 6). However, there is a problem in that this method allows variant hemoglobin to be separated but does not allow hemoglobin A1c to be separated. These problems apply to the general capillary electrophoresis method with respect to not only hemoglobin but also other samples.

[Patent Document 1] JP 2005-291926 A
[Patent Document 2] JP 4 (1992)-320957 A
[Patent Document 3] JP 5 (1993)-503989 A
[Patent Document 4] JP 8 (1996)-504037 A
[Patent Document 5] JP 9 (1997)-105739 A
[Patent Document 6] JP 2006-145537 A

DISCLOSURE OF THE INVENTION

Accordingly, the present invention is intended to provide a process for analyzing a sample by a capillary electrophoresis method that allows the apparatus to be reduced in size, allows a high analytical precision to be obtained, and can be carried out easily, as well as a capillary channel and a capillary electrophoresis apparatus that are used for the process.

In order to achieve the aforementioned object, an analytical process of the present invention is a process for analyzing a sample by a capillary electrophoresis method. The process includes a step of preparing a capillary channel to be used for the capillary electrophoresis method and step of performing electrophoretic separation of a complex of a sample and an anionic group-containing compound that are bonded together, in the capillary channel, wherein the capillary channel includes an A layer that is coated on an inner wall thereof and a B layer that is coated on the A layer.

A layer: a spacer layer formed of at least one selected from the group consisting of polydiallyldimethylammoniumchloride, a nonpolar polymer, and a cationic group-containing compound, wherein the polydiallyldimethylammoniumchloride is coated on the inner wall of the capillary channel by physical adsorption when the layer includes the polydiallyldimethylammoniumchloride, and at least one of the nonpolar polymer and the cationic group-containing compound is coated on the inner wall of the capillary channel by covalent bond when the layer includes at least one of the nonpolar polymer and the cationic group-containing compound B layer: an anionic layer formed of an anionic group-containing compound A capillary channel of the present invention is a capillary channel for capillary electrophoresis to be used for the analytical process of the present invention, wherein an A layer is coated on an inner wall of the capillary channel and a B layer is coated on the A layer.

A layer: a spacer layer formed of at least one selected from the group consisting of polydiallyldimethylammoniumchloride, a nonpolar polymer, and a cationic group-containing compound, wherein the polydiallyldimethylammoniumchloride is coated on the inner wall of the capillary channel by physical adsorption when the layer includes the polydiallyldimethylammoniumchloride, and at least one of the nonpolar polymer and the cationic group-containing compound is coated on the inner wall of the capillary channel by covalent bond when the layer includes at least one of the nonpolar polymer and the cationic group-containing compound B layer: an anionic layer formed of an anionic group-containing compound A capillary electrophoresis apparatus of the present invention is a capillary electrophoresis apparatus to be used for the analytical process of the present invention, wherein the capillary channel of the present invention is included. The capillary electrophoresis apparatus of the present invention may be a microchip electrophoresis apparatus with a reduced size (formed into a microchip) as described later.

In the analytical process of the present invention, the use of a capillary channel including a B layer that is formed via an A layer fixed to an inner wall thereof can prevent, for example, a protein in a blood sample, such as hemoglobin, from being adsorbed by the inner wall of the capillary channel. This makes it possible to generate a good electroosmotic flow. Furthermore, in the analytical process of the present invention, since a complex is generated by bonding a sample and an anionic group-containing compound, which then is performed electrophoretic separation, a higher separation efficiency is obtained as compared to the case where the sample alone is performed electrophoretic separation. Thus, according to the analytical process of the present invention, a sample such as hemoglobin can be analyzed in a short time with high precision. Moreover, since the A layer is fixed firmly to the inner wall of the capillary channel, once it is formed, it is not detached therefrom easily, even when being washed, which allows it to be used repeatedly. Accordingly, in the analytical process of the present invention, once the A layer is formed, it is not necessary to form the A layer every time an analysis is carried out, and thereby the analysis can be carried out easily. Furthermore, in the present invention, since the capillary electrophoresis method is employed, it is possible to reduce the size of the analysis apparatus.

BRIEF DESCRIPTION OF THE DRAWINGS

FIG. 6(A) is a plan view of the capillary electrophoresis apparatus of this example, FIG. 6(B) is a sectional view taken on line I-I shown in FIG. 6(A), and FIG. 6(C) is a sectional view taken on line II-II shown in FIG. 6(A).

BEST MODE FOR CARRYING OUT THE INVENTION

In the present invention, the term "running buffer" denotes a buffer solution (buffer) that is used in an actual separation process. Preferably, in the analytical process of the present invention, the B layer is formed on the A layer by contacting with a solution containing an anionic group-containing compound. In this state, it is preferable that the solution containing the anionic group-containing compound is a running buffer containing an anionic group-containing compound.

Preferably, in the analytical process of the present invention, the A layer made of polydiallyldimethylammoniumchloride is formed on the inner wall of the capillary channel by contacting with a solution containing the polydiallyldimethylammoniumchloride channel.

Preferably in the capillary channel to be used in the analytical process of the present invention, a sample is introduced into the running buffer containing the anionic group-containing compound, and voltage then is applied across both ends of the capillary channel to perform electrophoretic separation of a complex of the sample and the anionic group-containing compound.

In the analytical process and the capillary channel of the present invention, the anionic group-containing compound that forms the B layer may be the same as or different from the anionic group-containing compound that forms the complex together with the sample. Preferably, the anionic group-containing compound is an anionic group-containing polysaccharide. Examples of the anionic group-containing polysaccharide include sulfated polysaccharide, carboxylated polysaccharide, sulfonated polysaccharide, and phosphorylated polysaccharide. Among them, sulfated polysaccharide and carboxylated polysaccharide are preferable. The sulfated polysaccharide is preferably, for example, chondroitin sulfate or heparin, more preferably chondroitin sulfate. The carboxylated polysaccharide is preferably alginic acid or a salt thereof (for instance, sodium alginate). There are seven types of chondroitin sulfates A, B, C, D, E, H, and K and any of them may be used.

In the analytical process and the capillary channel of the present invention, it is preferable that the nonpolar polymer is a silicone polymer and the cationic group is at least one of an amino group and an ammonium group.

In the present invention, it is preferable that the sample contains hemoglobin.

The capillary electrophoresis apparatus of the present invention may include a substrate, a plurality of liquid reservoirs, and a capillary channel, wherein the plurality of liquid reservoirs may be formed in the substrate and may be allowed to communicate with one another through the capillary channel, and the capillary channel may be the capillary channel of the present invention. In this case, the substrate has a maximum length, for example, in the range of 10 to 100 mm, preferably in the range of 30 to 70 mm, a maximum width, for instance, in the range of 10 to 60 mm, and a maximum thickness, for example, in the range of 0.3 to 5 mm. The maximum length of the substrate is the length of the portion that is longest in the longitudinal direction of the substrate. The maximum width of the substrate is the length of the portion that is longest in the direction (width direction) perpendicular to the longitudinal direction of the substrate. The maximum thickness of the substrate is the length of the portion that is longest in the direction (thickness direction) perpendicular to both the longitudinal direction and the width direction of the substrate. As described above, the capillary electrophoresis apparatus of the present invention may be a microchip electrophoresis apparatus with a reduced size (formed into a microchip).

Next, the present invention is described in detail.

As described above, the capillary channel of the present invention is provided with the B layer that is formed on the inner wall thereof via the A layer.

The material for the capillary channel is not particularly limited. Examples thereof include glass, fused silica, and plastic. The inner wall of a capillary channel made of glass or fused silica usually has negative electric charges. The inner wall of a capillary channel made of plastic has positive or negative electric charges depending on the presence or absence and the type of the polar group contained in the plastic, or is uncharged (nonpolar). Even in the case of plastic having no polar group, introduction of a polar group allows it to have electric charges. A commercial product may be used as the capillary channel made of plastic. Examples of the capillary channel include those formed of, for example, polymethylmethacrylate, polycarbonate, polystyrene, polyethylene, polytetrafluoroethylene (PTFE), and polyether ether ketone (PEEK). The inner diameter of the capillary channel is, for example, in the range of 10 to 200 µm, preferably in the range of 25 to 100 µm. The length of the capillary channel is, for example, in the range of 10 to 1000 mm.

The A layer may be formed of one of polydiallyldimethylammoniumchloride, the nonpolar polymer, and the cationic group-containing compound, or may be formed of two or more of them.

When the A layer is formed on the inner wall of the capillary channel using polydiallyldimethylammoniumchloride, for example, a polydiallyldimethylammoniumchloride solution may be passed through the capillary channel. In a case where the capillary channel is made of glass or fused silica, the polydiallyldimethylammoniumchloride is adsorbed firmly to the inner wall of the capillary channel and thereby the A layer is formed. The A layer is not detached easily even when being washed. The concentration of the polydiallyldimethylammoniumchloride solution is, for example, in the range of 1 to 20 wt % and preferably in the range of 5 to 10 wt %. Preferably, the alkaline solution is passed through the capillary channel and then the distilled water is passed through the capillary channel to wash it before the polydiallyldimethylammoniumchloride solution is passed therethrough. An example of the alkaline solution includes, for example, an aqueous sodium hydroxide. Further, after the polydiallyldimethylammoniumchloride solution is passed through the capillary channel, it is preferable that the distilled water is passed through the capillary channel in order to remove residual polydiallyldimethylammoniumchloride that was not involved in a formation of the A layer.

As described above, the nonpolar polymer that forms the A layer on the inner wall of the capillary channel is preferably a silicone polymer. When the A layer is formed using the silicone polymer, for example, a solution containing the silicone polymer may be passed through the capillary channel. In a case where the capillary channel is made of glass or fused silica, the silicone polymer is fixed firmly to the inner wall of the capillary channel by a covalent bond and thereby the A layer is formed. The A layer is not detached easily even when being washed.

Examples of the silicone polymer include, for example, polysiloxane and polysilazane. Examples of the polysiloxane and the polysilazane include, for example, polydiorganosiloxane, polydiorganosilazane, and polyorganohydrosiloxane. Specific examples of the polysiloxane and the polysilazane include polydialkylsiloxane, polydialkylsilazane, polyarylsiloxane, polyarylsilazane, polyalkylarylsiloxane, polydiarylsiloxane, cyclic siloxane, and cyclic silazane.

The solution containing the silicone polymer is, for example, a dispersed solution containing the silicone polymer dispersed in a solvent, or a dissolved solution containing the silicone polymer dissolved in a solvent. After the dispersed solution or the dissolved solution of the silicone polymer is passed through the capillary channel, when the solvent is evaporatively removed by drying, a film layer of the silicone polymer is formed on the inner wall of the capillary channel. When it is heated, the silicone polymer is bonded to the inner wall of the capillary channel made of glass or fused silica by the covalent bond. For example, the heating treatment preferably is carried out as follows. First, inert gas is passed through the capillary channel, in which the film layer of the silicone polymer is formed, to remove oxygen. In this state, both ends of the capillary channel are sealed by heating or the like. When the capillary channel in this state is heated, for example, at 200 to 450° C. for 10 minutes to 12 hours, the silicone polymer is bonded to the inner wall of the capillary channel by the covalent bond. Subsequently, the capillary channel is cooled and the both ends thereof are opened by cutting or the like, and then unreacted silicone polymer is removed by washing therein with the solvent. In this manner, the A layer made of the silicone polymer is formed on the inner wall of the capillary channel. The A layer made of the silicone polymer has a thickness of, for example, in the range of 50 to 400 nm and preferably in the range of 100 to 400 nm. A commercial product may be used as the capillary channel that includes the A layer formed of the silicone polymer.

When the A layer is formed on the inner wall of the capillary channel with the cationic group-containing compound, for example, a compound containing the cationic group and a reaction group may be used. In a case where the capillary channel is made of glass or fused silica, a compound (a silylation agent) including the cationic group and silicon may be used. Preferable examples of the cationic group include an amino group and an ammonium group. Further, a preferable example of the cationic group-containing compound includes the silylation agent that contains at least one of the cationic group of amino group and the ammonium group. The amino group may be a primary amino group, a secondary amino group, or a tertiary amino group.

Examples of the silylation agent include N-(2-diaminoethyl)-3-propyltrimethoxysilane, aminophenoxydimethylvinylsilane, 3-aminopropyldiisopropylethoxysilane, 3-aminopropylmethylbis(trimethylsiloxy)silane, 3-aminopropylpentamethyldisiloxane, 3-aminopropylsilanetriol, bis(P-aminophenoxy)dimethylsilane, 1,3-bis(3-aminopropyl)tetramethyldisiloxane, bis(dimethylamino)dimethylsilane, bis(dimethylamino) vinylmethylsilane, bis(2-hydroxyethyl)-3-aminopropyltriethoxysilane, 3-cyanopropyl(diisopropyl)dimethylaminosilane, (aminoethylaminomethyl)phenethyltrimethoxysilane, N-methylaminopropyltriethoxysilane, tetrakis(diethylamino)silane, tris(dimethylamino)chlorosilane, tris(dimethylamino)silane.

For the silylation agent, one obtained by substituting the silicon atom with titanium or zirconium may be used. One silylation agent may be used alone or two or more of them may be used in combination.

The A layer is formed using the silylation agent, for example, as follows. First, a silylation agent is dissolved or dispersed in an organic solvent and thereby a treatment liquid is prepared. The organic solvent to be used for preparing the treatment liquid can be, for example, dichloromethane or toluene. The concentration of the silylation agent of the treatment liquid is not particularly limited. This treatment liquid is passed through a capillary channel made of glass or fused silica and is heated. This heating allows the silylation agent to be bonded to the inner wall of the capillary channel by a covalent bond. As a result, the cationic group is placed on the inner wall of the capillary channel. Thereafter, it is washed with at least one of an organic solvent (for instance, dichloromethane, methanol, or acetone), an acid solution (for example, phosphoric acid), an alkaline solution, and a surfactant solution (aftertreatment). Preferably, this washing is carried out, although it is optional. A commercial product may be used as the capillary channel that includes the A layer formed of the silylation agent.

Next, the B layer is formed on the A layer with the anionic group-containing compound. The B layer may be formed on the A layer by contacting with the solution containing the anionic group-containing compound. In this case, a solution for forming the B layer may be prepared separately, however, from an aspect of the operation efficiency, it is preferable that a running buffer containing the anionic group-containing compound is prepared and is passed through the capillary channel that is provided with the A layer.

The running buffer is not particularly limited, but a buffer containing acid used therein is preferred. Examples of the acid include maleic acid, tartaric acid, succinic acid, fumaric acid, phthalic acid, malonic acid, and malic acid. Preferably, the running buffer contains a weak base. Examples of the weak base include arginine, lysine, histidine, and tris. The running buffer has a pH, for example, in the range of 4.5 to 6. The types of the buffer of the running buffer include MES, ADA, ACES, BES, MOPS, TES, and HEPES. In the running buffer, the anionic group-containing compound has a concentration, for example, in the range of 0.01 to 5 wt %.

The analytical process of the present invention can be carried out with respect to, for example, a sample containing hemoglobin as follows.

The analytical process using the capillary channel that includes the A layer formed of polydiallyldimethylammoniumchloride is explained. First, a capillary channel made of glass or fused silica is prepared. Next, the alkaline solution such as an aqueous sodium hydroxide is passed through the capillary channel under pressure applied by, for example, a pump. Subsequently, the distilled water is passed through the capillary channel and thereby it is washed. The time for which each of the alkaline solution and the distilled water is passed therethrough is respectively, for example, 1 to 10 minutes, and the pressure when each of the alkaline solution and the distilled water is passed therethrough is respectively, for example, 0.05 to 0.1 MPa. Next, a polydiallyldimethylammoniumchloride solution is passed through the capillary channel under pressure applied by, for example, a pump. The time for which the polydiallyldimethylammoniumchloride solution is passed therethrough is, for example, 5 to 30 minutes, and the pressure when the polydiallyldimethylammoniumchloride solution is passed therethrough is, for example, 0.05 to 0.1 MPa. Then, the distilled water is passed through the capillary channel under pressure applied by, for example, a pump to remove the residual polydiallyldimethylammoniumchloride. The time for which the distilled water is passed therethrough and the pressure when the distilled water is passed therethrough is as same as in the case of the aforementioned washing. In this manner, the A layer made of the polydiallyldimethylammoniumchloride is formed on the inner wall of the capillary channel. In this state, the time and the pressure are determined suitably according to an inner diameter and a length of the capillary channel. Each time and pressure mentioned above is an example which is preferable for the capillary channel that has the inner diameter of 50 μm and the length of 320 mm. The same applies to the following.

Next, a running buffer containing an anionic group-containing compound such as chondroitin sulfate is passed through the capillary channel under pressure applied by, for example, a pump. The time for which the running buffer is passed therethrough is, for example, 10 to 60 minutes, and the pressure when the running buffer is passed therethrough is, for example, 0.05 to 0.1 MPa. As a result, a B layer formed of chondroitin sulfate is coated on the A layer. In this state, a hemoglobin-containing sample is introduced into the capillary channel, and voltage then is applied across both ends of the capillary channel to carry out electrophoresis. The hemoglobin-containing sample is not particularly limited and is, for example, a sample obtained by hemolyzing whole blood. This sample may be diluted with distilled water or a running buffer. The hemoglobin-containing sample is introduced from the anode side of the capillary channel. The hemoglobin thus introduced forms a complex by being bonded with the anionic group-containing compound contained in the running buffer. The applied voltage generates an electroosmotic flow in the running buffer contained in the capillary channel and thereby the complex is transferred toward the cathode side of the capillary channel. The voltage applied is, for example, in the order of 5 to 30 kV. This transfer is detected by an optical method. The detection made by the optical method is not particularly limited. Preferably, it is carried out at a wavelength of 415 nm.

The analytical process using the capillary channel that includes the A layer formed of at least one of the nonpolar polymer and the cationic group-containing compound can be carried out in the same manner as described above except that the capillary channel that includes the A layer formed in the aforementioned manner is prepared.

In the present invention, the hemoglobin to be analyzed is not particularly limited. Examples thereof include normal hemoglobin, glycated hemoglobin (for instance, HbA1c, labile HbA1c, and GHbLys), and hemoglobin variants. In the present invention, it is possible to separate HbA1c and hemoglobin other than that from each other to analyze them.

Next, the capillary electrophoresis apparatus of the present invention is described using examples. However, the capillary electrophoresis apparatus of the present invention is not limited to the following examples.

Figure 6:
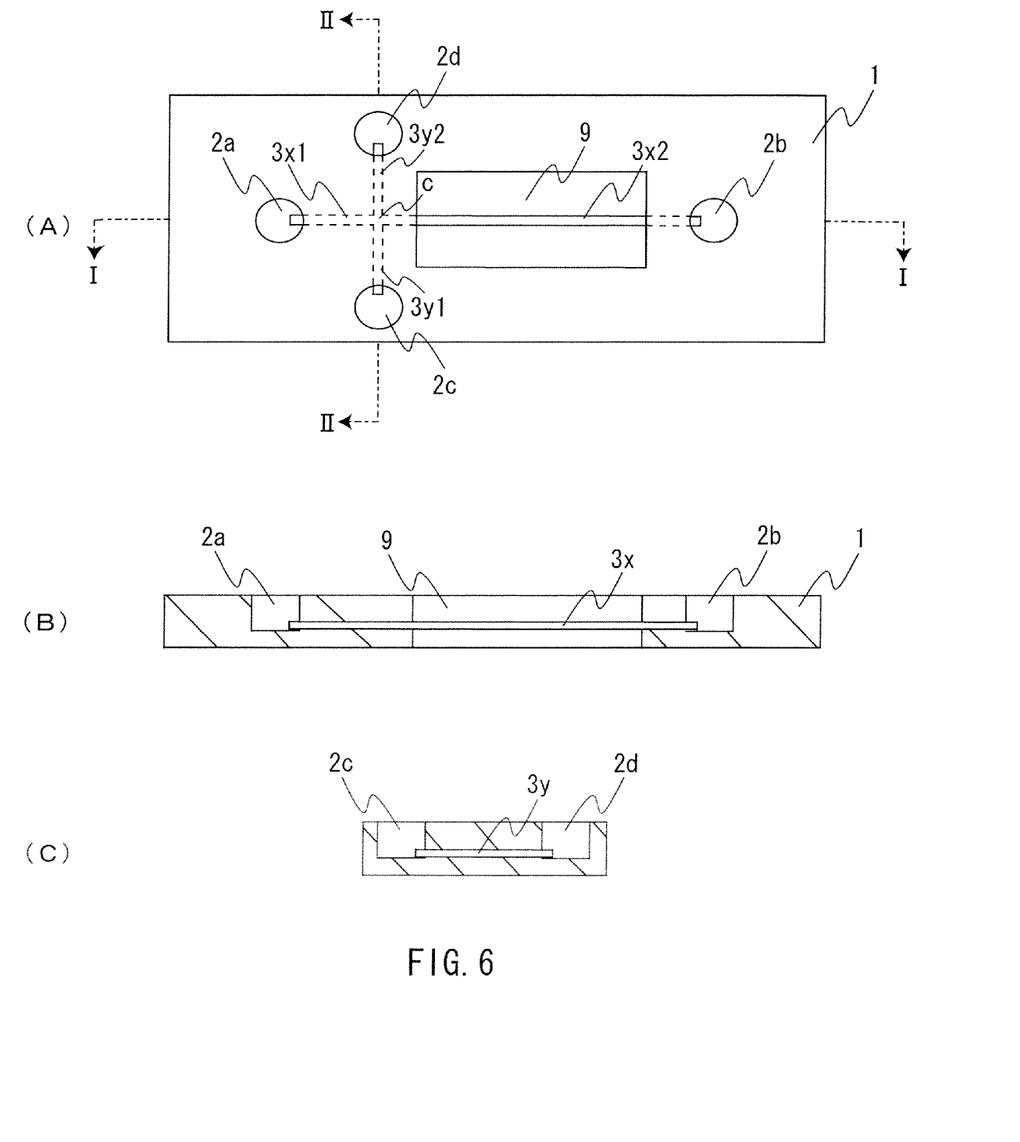
FIG. 6 shows diagrams illustrating the configuration of an example of the capillary electrophoresis apparatus of the present invention.

FIG. 6 shows an example of the capillary electrophoresis apparatus according to the present invention. FIG. 6(A) is a plan view of the capillary electrophoresis apparatus of this example, FIG. 6(B) is a sectional view taken on line II shown in FIG. 6(A), and FIG. 6(C) is a sectional view taken on line II-II shown in FIG. 6(A). In those figures, for ease of understanding, for example, the sizes and ratios of the respective components are different from actual ones. The capillary electrophoresis apparatus of this example is a microchip electrophoresis apparatus with a reduced size (formed into a microchip). As shown in the figures, this microchip electrophoresis apparatus includes a substrate 1, a plurality (four in this example) of liquid reservoirs 2a to 2d, and four capillary channels 3x1, 3x2, 3y1, and 3y2. All of the four capillary channels are capillary channels of the present invention. The four liquid reservoirs 2a to 2d include a first introduction reservoir 2a, a first recovery reservoir 2b, a second introduction reservoir 2c, and a second recovery reservoir 2d. In the four capillary channels, first ends thereof meet at the central portion c to be joined together in a cross shape. Accordingly, the four capillary channels communicate with one another at their inner parts. The substrate 1 is provided with a cavity for inserting the four capillary channels thereinto (not shown in the figures). The capillary channel 3x1 is inserted into the substrate 1 so that the other end thereof is located at the bottom surface of the first introduction reservoir 2a. The capillary channel 3x2 is inserted into the substrate 1 so that the other end thereof is located at the bottom surface of the first recovery reservoir 2b. The capillary channels 3x1 and 3x2 form a capillary channel 3x for sample analysis. The capillary channel 3y1 is inserted into the substrate 1 so that the other end thereof is located at the bottom surface of the second introduction reservoir 2c. The capillary channel 3y2 is inserted into the substrate 1 so that the other end thereof is located at the bottom surface of the second recovery reservoir 2d. The capillary channels 3y1 and 3y2 form a capillary channel 3y for sample introduction. The plurality of liquid reservoirs 2a to 2d each are formed as a concave part in the substrate 1. The substrate 1 has a rectangular parallelepiped opening (window) 9 on the first recovery reservoir 2b side with respect to the capillary channel 3y for sample introduction. The microchip electrophoresis apparatus of this example is rectangular parallelepiped. However, the present invention is not limited thereto. The microchip electrophoresis apparatus of the present invention may have any shape as long as it does not cause any problems in the electrophoresis measurement. The planar shape of the microchip electrophoresis apparatus of this example is rectangular. However, the present invention is not limited thereto. The planar shape of the microchip electrophoresis apparatus of the present invention may be, for example, square or another shape. In the microchip electrophoresis apparatus of this example, the capillary channel 3x for sample analysis is different in maximum length from the capillary channel 3y for sample introduction. However, the present invention is not limited thereto. In the microchip electrophoresis apparatus of the present invention, the maximum length of the capillary channel 3x for sample analysis may be identical to that of the capillary channel 3y for sample introduction. Similarly with respect to items other than those described above, the configuration of the microchip electrophoresis apparatus of the present invention is not limited to this example.

Next, the process for producing the microchip electrophoresis apparatus of this example is described. However, the microchip electrophoresis chip may be produced by a process other than the production process described below.

In the microchip electrophoresis apparatus of this example, the substrate 1 to be used can be one formed of, for example, a glass or polymer material. Examples of the glass material include synthetic silica glass, and borosilicate glass. Examples of the polymer material include polymethylmethacrylate (PMMA), cycloolefin polymer (COP), polycarbonate (PC), polydimethylsiloxane (PDMS), polystyrene (PS), and polylactic acid.

In the microchip electrophoresis apparatus of this example, the maximum length, maximum width, and maximum thickness of the substrate 1 are as described above.

The inner diameters of the four capillary channels are the same as that of the capillary channel of the present invention. The capillary channel 3x for sample analysis and the capillary channel 3y for sample introduction each have a maximum length, for example, in the range of 0.5 to 15 cm. The respective lengths of the four capillary channels are determined according to the maximum lengths of the capillary channel 3x for sample analysis and the capillary channel 3y for sample introduction.

The volumes of the plurality of liquid reservoirs 2a to 2d are not particularly limited. For example, each of them has a volume of 1 to 1000 mm$^3$, preferably in the range of 50 to 100 mm$^3$. In FIG. 6, the shapes of the plurality of liquid reservoirs 2a to 2d are cylindrical. However, the present invention is not limited thereto. In the microchip electrophoresis apparatus of the present invention, the shapes of the plurality of liquid reservoirs are not particularly limited as long as they do not cause any problems in introduction and recovery of the sample described later. For example, each of them may have an arbitrary shape, such as a quadrangular prism shape, a quadrangular pyramidal shape, a conical shape, or a shape formed by combining them. Furthermore, the volumes and shapes of the plurality of liquid reservoirs may be identical to or different from one another.

An example of the process of producing a microchip electrophoresis apparatus of this example is described below. However, the microchip electrophoresis apparatus may be produced by a process other than the production process described below.

First, the substrate 1 is produced. The methods of forming the four liquid reservoirs 2a to 2d and the opening (window) 9 in the substrate 1 are not particularly limited. For example, when the material used for the substrate 1 is the aforementioned glass, the formation method can be, for instance, ultrasonic machining. For example, when the material used for the substrate 1 is the aforementioned polymer material, the formation method can be, for instance, a cutting method or a molding method such as injection molding, cast molding, or press molding that employs a mold. The four liquid reservoirs 2a to 2d and the opening (window) 9 each may be formed independently, or all of them may be formed simultaneously. When the four liquid reservoirs 2a to 2d and the opening (window) 9 each are formed independently, they may be formed in any order. It is preferable that all the four liquid reservoirs 2a to 2d and the opening (window) 9 be formed simultaneously by, for example, a method that employs a mold, since the number of the steps is smaller in this case.

Next, the four capillary channels are inserted into the substrate 1. Thus, a microchip electrophoresis apparatus of this example can be obtained.

Figure 7:
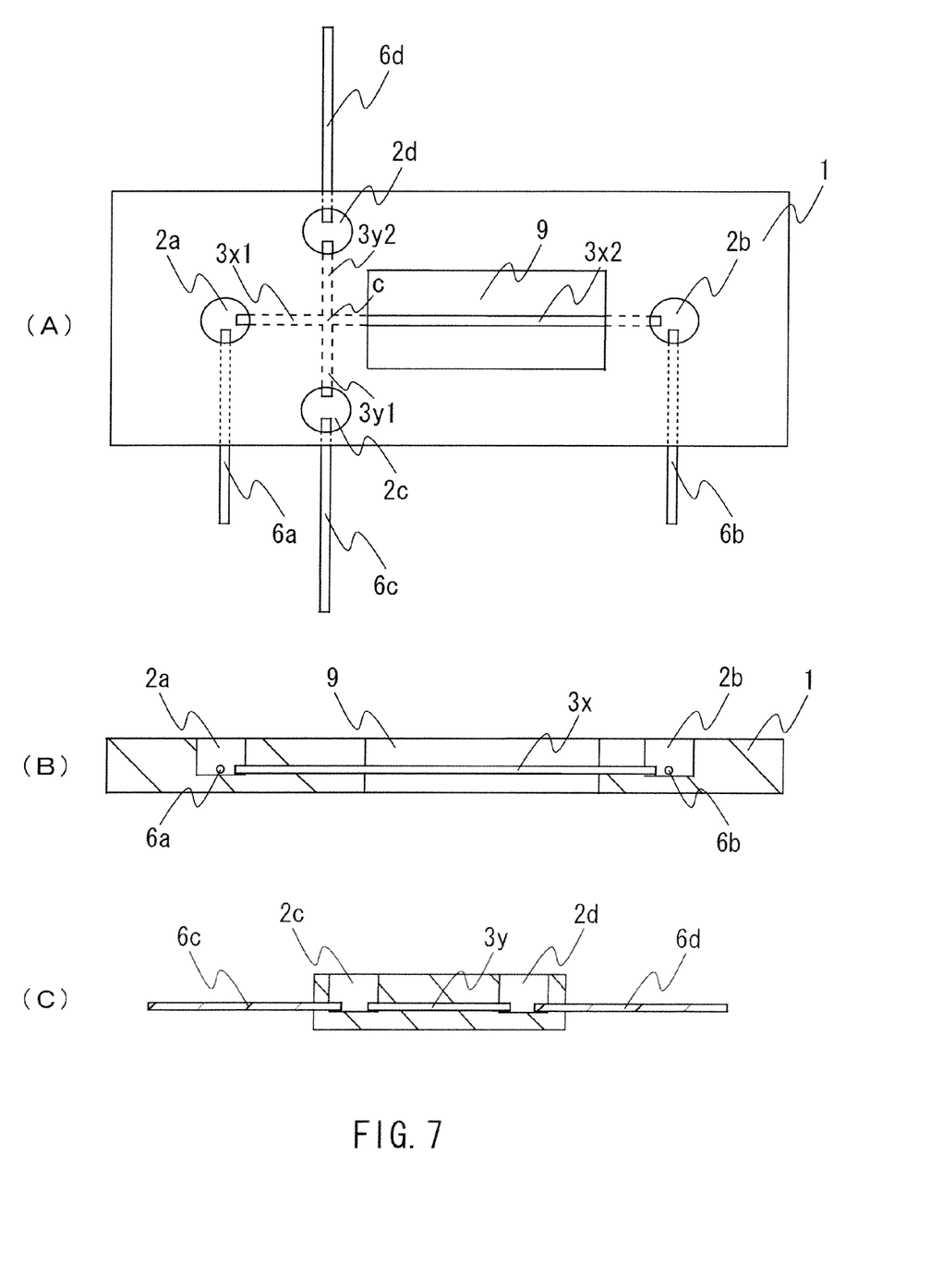
FIG. 7 shows diagrams illustrating the configuration of another example of the capillary electrophoresis apparatus of the present invention.

The microchip electrophoresis apparatus further may include a plurality of electrodes. FIG. 7 shows a microchip electrophoresis apparatus of this example that includes the plurality of electrodes. In FIG. 7, the identical parts to those shown in FIG. 6 are indicated with identical numerals and symbols. As shown in FIG. 7, this microchip electrophoresis apparatus has four electrodes 6a to 6d. The four electrodes 6a to 6d are buried in the substrate 1 in such a manner that first ends thereof are located inside the plurality of liquid reservoirs 2a to 2d, respectively. The four electrodes 6a to 6d can be disposed easily when, for example, holes for introducing the four electrodes 6a to 6d are formed in the side faces of the substrate 1 in producing the substrate 1. In the microchip electrophoresis apparatus, the plurality of electrodes are optional components. For example, the plurality of electrodes may be inserted into the plurality of liquid reservoirs when the microchip electrophoresis apparatus is used.

The plurality of electrodes 6a to 6d may be any electrodes, as long as they can be used for the electrophoresis method. The plurality of electrodes 6a to 6d each are, for example, an electrode made of stainless steel (SUS), a platinum (Pt) electrode, or a gold (Au) electrode.

The microchip electrophoresis apparatus further may include a pretreatment reservoir for hemolyzing a sample containing hemoglobin and diluting it. The treatment for hemolyzing the hemoglobin-containing sample is not particularly limited. For example, it may be a treatment for hemolyzing the hemoglobin-containing sample with a hemolytic agent. The hemolytic agent destroys, for example, a blood cell membrane of a blood cell component in the hemoglobin-containing sample. Examples of the hemolytic agent include the aforementioned running buffer, saponin, and "Triton X-100" (trade name) manufactured by Nacalai Tesque, Inc. Particularly preferable is the running buffer. Preferably, the pretreatment reservoir communicates with, for example, the introduction reservoirs. The pretreatment reservoir may be formed in a suitable place such as a place near the liquid reservoir with which it communicates, for example, the second introduction reservoir 2c. When the pretreatment reservoir is provided, the hemoglobin-containing sample is introduced into the pretreatment reservoir. The hemoglobin-containing sample thus pretreated is introduced into a liquid reservoir that communicates with the pretreatment reservoir, for example, the second introduction reservoir 2c through the channel connecting the pretreatment reservoir and the second introduction reservoir 2c. The pretreatment reservoir may have a configuration in which two reservoirs, a reservoir for hemolyzing the hemoglobin-containing sample and a reservoir for diluting the hemoglobin-containing sample, are in communication with each other.

Figure 8:
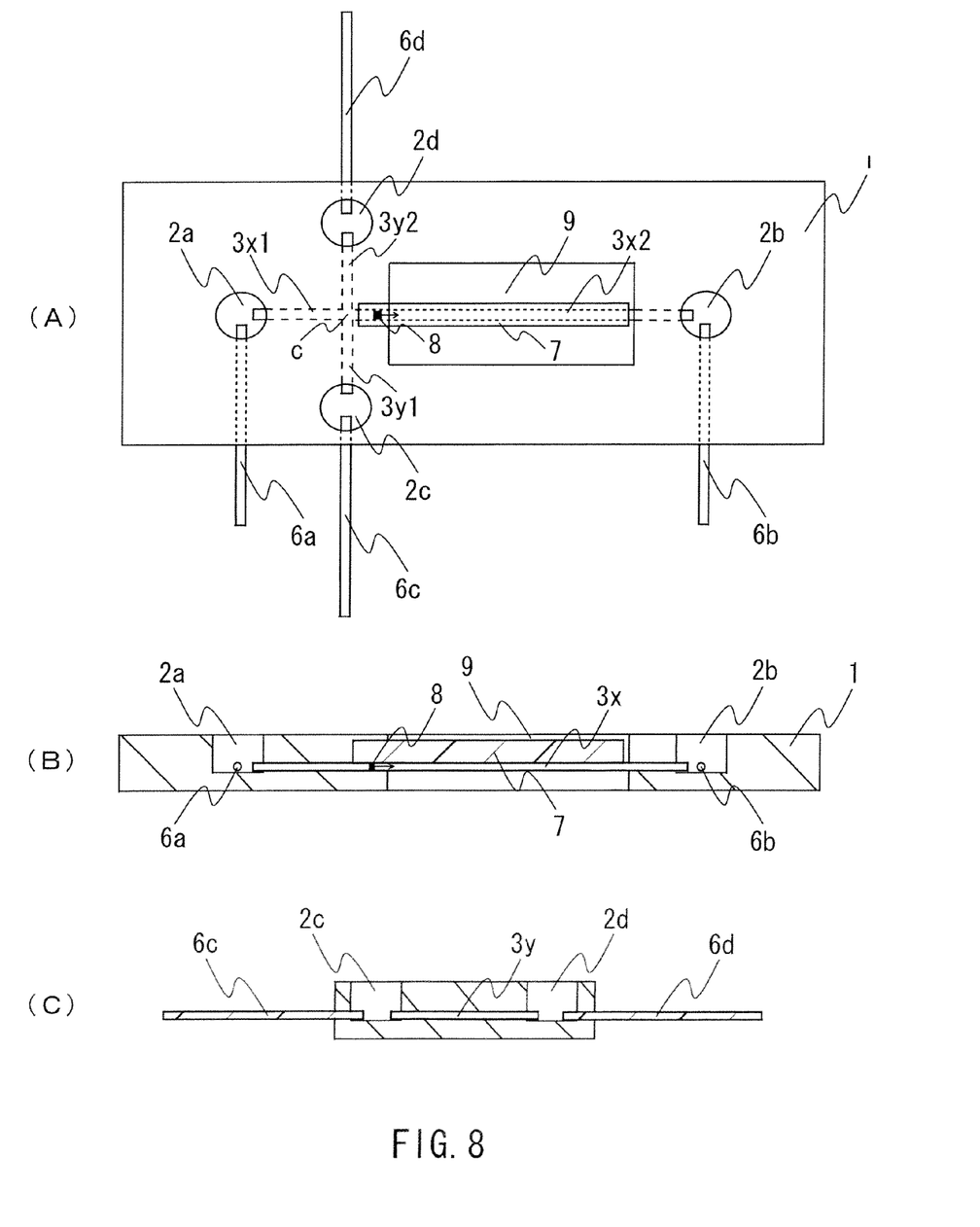
FIG. 8 shows diagrams illustrating the configuration of still another example of the capillary electrophoresis apparatus of the present invention.

The microchip electrophoresis apparatus further may include an analysis unit. FIG. 8 shows a microchip electrophoresis apparatus of this example including the analysis unit. In FIG. 8, identical parts to those shown in FIGS. 6 and 7 are indicated with identical numerals and symbols. As shown in FIG. 8, this microchip electrophoresis apparatus includes an analysis unit 7. In the microchip electrophoresis apparatus of this example, the analysis unit 7 is a detector (line detector). The line detector is disposed directly on the capillary channel 3x2 in such a manner that it is located on the first recovery reservoir 2b side with respect to the intersection part between the capillary channel 3x for sample analysis and the capillary channel 3y for sample introduction. In this microchip electrophoresis apparatus, the substrate 1 is provided with a cavity into which the analysis unit (line detector) 7 is to be inserted, in addition to the cavity into which the four capillary channels are to be inserted (not shown in the figures). The line detector has a light source and a detection unit built-in. The line detector emits light from the light source towards the sample to detect light reflected from the sample in the detection unit, and thereby measures absorbance. The analysis unit 7 is not limited to the line detector. It may be any analysis unit as long as, for example, it can analyze a sample containing hemoglobin. For example, the analysis unit 7 may be configured with a light source disposed under the microchip electrophoresis apparatus and a detection unit disposed in a place corresponding to the place where the line detector is disposed. In this case, light is emitted from the light source toward the sample, the transmitted light from the sample is detected in the detection unit, and thus absorbance is measured.

Figure 9:
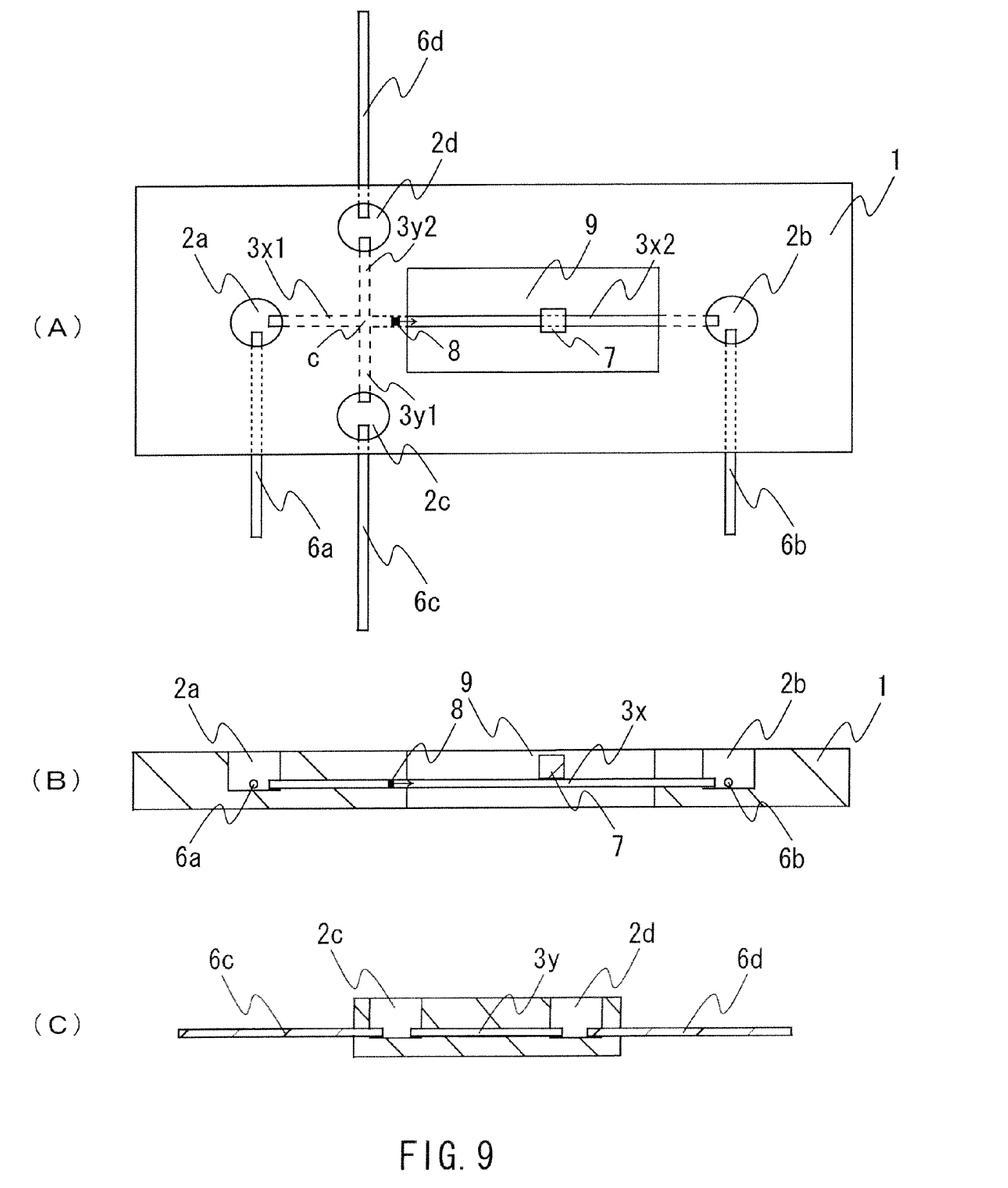
FIG. 9 shows diagrams illustrating the configuration of yet another example of the capillary electrophoresis apparatus of the present invention.

FIG. 9 shows still another example of the microchip electrophoresis apparatus according to the present invention. In FIG. 9, identical parts to those shown in FIG. 8 are indicated with identical numerals and symbols. As shown in FIG. 9, the microchip electrophoresis apparatus of this example has the same configuration as that of the microchip electrophoresis apparatus shown in FIG. 8 except that the analysis unit 7 is different. As in this example, the analysis unit 7 may measure the absorbance at one point.

The analytical processes of the present invention using the microchip electrophoresis apparatuses shown in FIGS. 8 and 9 can be carried out with respect to, for example, a sample containing hemoglobin, as follows.

The analitical processes in a case in which the capillary channel that includes the A layer formed of polydiallyldimethylammoniumchloride is used for the aforementioned four capillary channels is explained. First, an alkaline solution such as an aqueous sodium hydroxide is passed through the capillary channel 3x for sample analysis and the capillary channel 3y for sample introduction under pressure applied by, for example, a pump. Subsequently, distilled water is passed through the capillary channel 3x for sample analysis and the capillary channel 3y for sample introduction to wash them. The time for which each of the alkaline solution and the distilled water is passed therethrough and the pressure applied when each of them is passed therethrough are, for example, as described above. Next, the polydiallyldimethylammoniumchloride solution is passed through the capillary channel 3x for sample analysis and the capillary channel 3y for sample introduction under pressure applied by, for example, a pump. The time for which it is passed therethrough and the pressure thereof are, for example, as described above. Then, distilled water is passed through the capillary channel 3x for sample analysis and the capillary channel 3y for sample introduction under pressure applied by, for example, a pump to remove residual polydiallyldimethylammoniumchloride. The time for which it is passed therethrough and the pressure thereof are, for example, as described above. In this manner, the A layer is formed on the inner wall of the capillary channel 3x for sample analysis and the capillary channel 3y for sample introduction with the polydiallyldimethylammoniumchloride.

Next, a running buffer containing an anionic group-containing polysaccharide such as chondroitin sulfate is passed through the capillary channel 3x for sample analysis and the capillary channel 3y for sample introduction under pressure applied by, for example, a pump. The time for which it is passed therethrough and the pressure thereof are, for example, as described above. Thereby, the B layer made of such as chondroitin sulfate is coated on the A layer. Thereafter, the capillary channel 3x for sample analysis and the capillary channel 3y for sample introduction are filled with the running buffer by pressure or capillary action.

It is preferable that when the microchip electrophoresis apparatus is not in use (when no analysis is carried out), the step of filling them with the running buffer be completed beforehand, since it makes it possible to omit the respective steps described above and to proceed directly to the following step.

Subsequently, a hemoglobin-containing sample is introduced into the second introduction reservoir 2c. Examples of the hemoglobin-containing sample are as described above. When the microchip electrophoresis apparatus has the pretreatment reservoir (not shown in the figures), the hemoglobin-containing sample is introduced into the pretreatment reservoir and is pretreated there. Subsequently, voltage is applied to the electrode 6c and the electrode 6d to generate a potential difference between the ends of the capillary channel 3y for sample introduction. Thus, the hemoglobin-containing sample is introduced into the capillary channel 3y for sample introduction. The hemoglobin thus introduced is bonded with an anionic group-containing polysaccharide contained in the running buffer to form a complex. Voltage is applied to generate an electroosmotic flow in the running buffer contained in the capillary channel 3y for sample introduction and thereby the complex is transferred to the intersection part between the capillary channel 3x for sample analysis and the capillary channel 3y for sample introduction.

The potential difference between the electrode 6c and the electrode 6d is, for instance, in the range of 0.5 to 5 kV Next, voltage is applied to the electrode 6a and the electrode 6b to generate a potential difference between the ends of the capillary channel 3x for sample analysis. In this manner, the capillary channel having a potential difference between the ends thereof is changed momentarily from the capillary channel 3y for sample introduction to the capillary channel 3x for sample analysis, so that as shown with arrows in FIGS. 8 and 9, the sample 8 is transferred to the first recovery reservoir 2b side from the intersection part between the capillary channel 3x for sample analysis and the capillary channel 3y for sample introduction.

The potential difference between the electrode 6a and the electrode 6b is, for example, in the range of 0.5 to 5 kV.

Subsequently, the respective components of the hemoglobin-containing sample separated due to the difference in transfer rate are detected with the detector 7. Thus, the respective components of the hemoglobin-containing sample can be separated to be analyzed.

The analytical processes in a case in which the capillary channel that includes the A layer formed of at least one of the nonpolar polymer and the cationic group-containing compound is used for the aforementioned four capillary channels can be carried out in the same manner as described above except that the capillary channel that includes the A layer formed in the aforementioned manner is used.

Next, examples of the present invention are described.

Example 1

Figure 1:
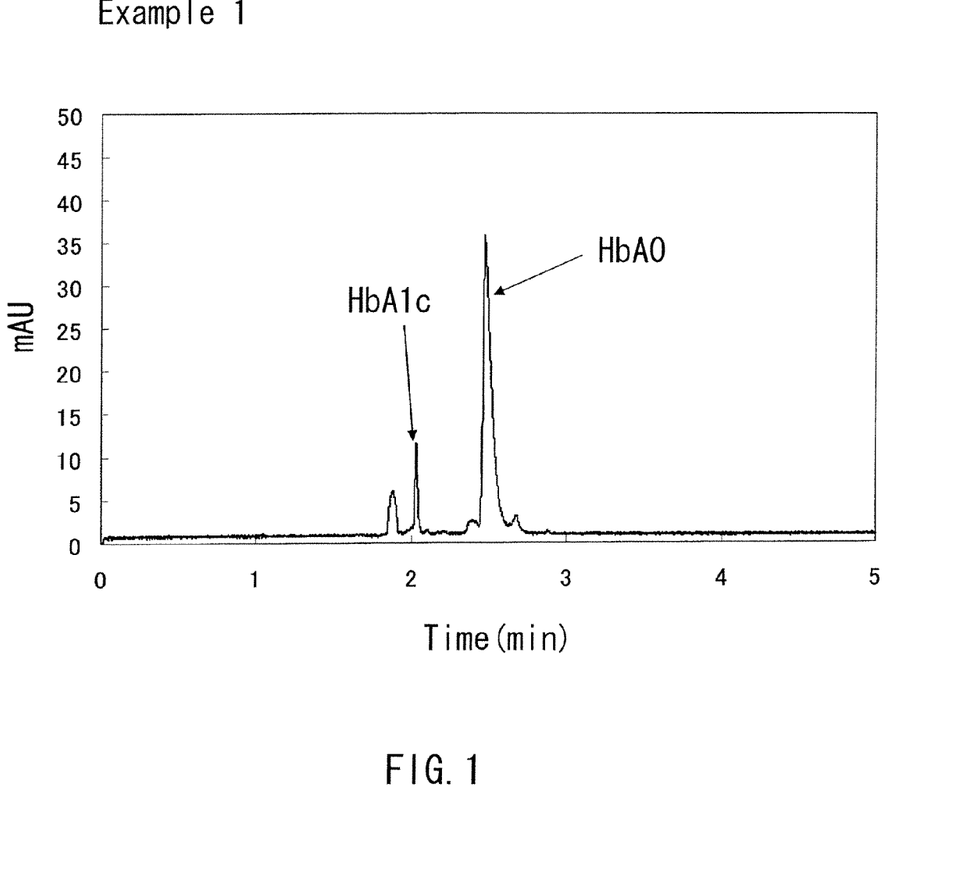
FIG. 1 is an electropherogram showing the result of analysis of hemoglobin in an example of the present invention.

A capillary channel (with an overall length of 32 cm, an effective length of 8.5 cm, and an inner diameter of 50 μm) made of fused silica was prepared. An aqueous sodium hydroxide (1 mol/L) was passed through this capillary channel at a pressure of 0.1 MPa (1000 mbar) for 10 minutes. Subsequently; distilled water was passed through this capillary channel at the same pressure as described above for 20 minutes to wash it. Then, a polydiallyldimethylammoniumchloride solution (10 wt %) was passed through the capillary channel at the same pressure as described above for 30 minutes. Subsequently, distilled water was passed through the capillary channel at the same pressure as described above for 20 minutes to form the A layer made of polydiallyldimethylammoniumchloride on the inner wall of the capillary channel. Then, a running buffer (pH 5.5) was prepared that contains chondroitin sulfate added to 100 mM malic acid and an arginine acid aqueous solution at a ratio of 0.5 wt %. This running buffer was passed through the capillary channel, in which the A layer is formed, at the same pressure as described above, and thereby the B layer is formed on the A layer. With the capillary channel being filled with the running buffer, a sample containing hemoglobin dissolved in distilled water was injected into the capillary channel. Thereafter, a voltage of 10 kV was applied across both ends of the capillary channel, and thereby electrophoresis was carried out. The hemoglobin-containing sample was injected into the capillary channel from the anode side thereof. The hemoglobin that had been transferred was detected at an absorbance of 415 nm. This result is shown in the electropherogram in FIG. 1. As shown in FIG. 1, in this example, it was possible to detect normal hemoglobin (HbA0) and glycated hemoglobin (HbA1c) separately. Furthermore, as for the capillary channel used in this example, because the B layer was formed simply by passing through the running buffer therein after being washed, it was possible to carry out the analysis immediately.

Example 2

Figure 2:
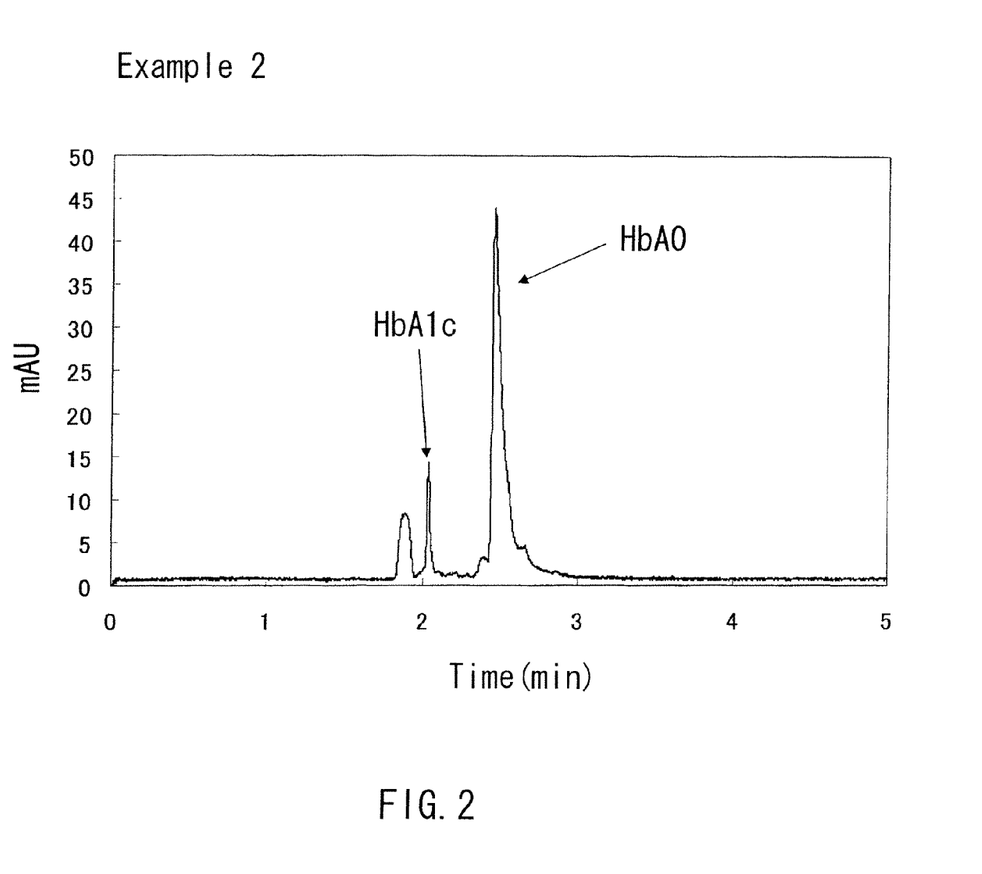
FIG. 2 is an electropherogram showing the result of analysis of hemoglobin in another example of the present invention.

A capillary channel (with an overall length of 32 cm, an effective length of 8.5 cm, and an inner diameter of 50 μm) made of fused silica was prepared. The capillary channel had an A layer formed with a silylation agent having an amino group that was fixed to the inner wall thereof by a covalent bond. Distilled water was passed through this capillary channel at a pressure of 0.1 MPa (1000 mbar) for 20 minutes to wash it. Then, a running buffer (pH 5.5) was prepared that contains chondroitin sulfate added to 100 mM malic acid and an arginine acid aqueous solution at a ratio of 0.5 wt %. This running buffer was passed through the capillary channel at the same pressure as described above, and thereby the B layer was formed on the A layer. With the capillary channel being filled with the running buffer, a sample containing hemoglobin dissolved in distilled water was injected into the capillary channel. Thereafter, a voltage of 10 kV was applied across both ends of the capillary channel, and thereby electrophoresis was carried out. The hemoglobin-containing sample was injected into the capillary channel from the anode side thereof. The hemoglobin that had been transferred was detected at an absorbance of 415 nm. This result is shown in the electropherogram in FIG. 2. As shown in FIG. 2, in this example, it was possible to detect normal hemoglobin (HbA0) and glycated hemoglobin (HbA1c) separately. Furthermore, as for the capillary channel used in this example, because the B layer was formed simply by passing through the running buffer therein after being washed, it was possible to carry out the analysis immediately. In this state, the same analysis was carried out 10 times with the same sample as described above to evaluate precision. This result is shown in the following Table 1. In Table 1, a relative area (%) denotes a ratio (%) of each peak area of the normal hemoglobin (HbA0) and the glycated hemoglobin (HbA1c) relative to a total peak area. As shown in Table 1, a value of coefficient of variation (CV) is small in each of the normal hemoglobin (HbA0) and the glycated hemoglobin (HbA1c). Thereby, it can be said that the analytical processes of the present invention is excellent in the repeatability.

TABLE 1

| No. | Relative Area (%) | |
| --- | --- | --- |
| | HbA1c | HbA0 |
| 1 | 10.08 | 89.92 |
| 2 | 10.37 | 89.63 |
| 3 | 10.18 | 89.82 |
| 4 | 10.49 | 89.51 |
| 5 | 10.34 | 89.66 |
| 6 | 10.30 | 89.70 |
| 7 | 9.89 | 90.11 |
| 8 | 10.17 | 89.83 |
| 9 | 10.24 | 89.76 |
| 10 | 10.32 | 89.68 |
| Average | 10.24 | 89.76 |
| Coefficient of Variation(CV) | 1.7 | 0.2 |

Example 3

Figure 3:
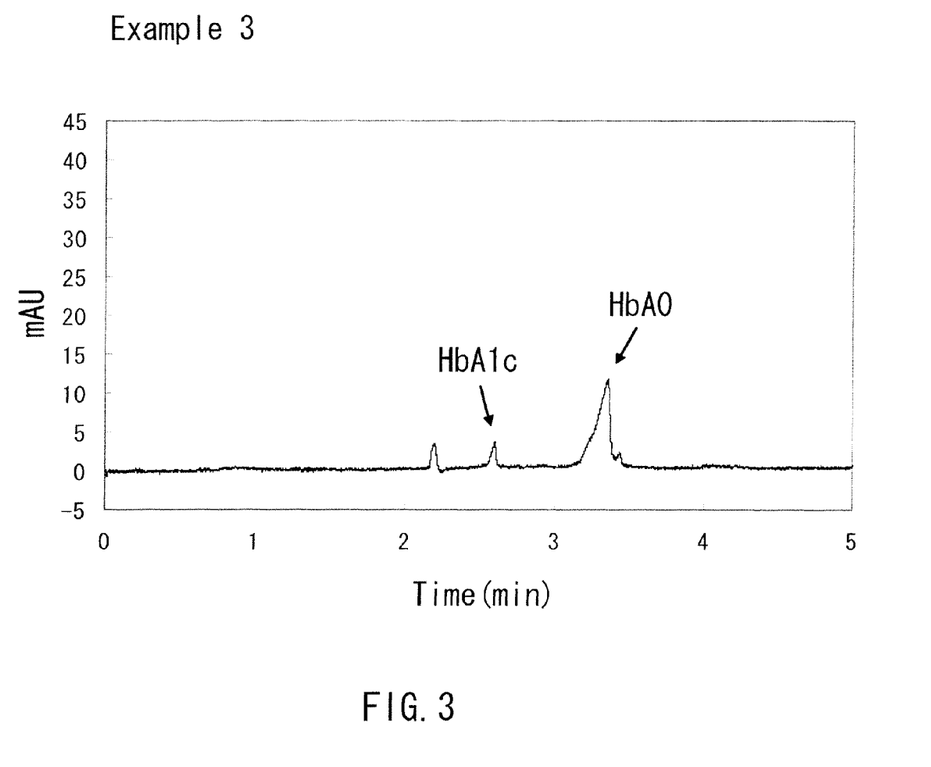
FIG. 3 is an electropherogram showing the result of analysis of hemoglobin in still another example of the present invention.

A capillary channel (with an overall length of 32 cm, an effective length of 8.5 cm, and an inner diameter of 50 μm) made of fused silica was prepared. The capillary channel had an A layer formed with a silylation agent having an amino group that was fixed to the inner wall thereof by a covalent bond. Distilled water was passed through this capillary channel at a pressure of 0.1 MPa (1000 mbar) for 20 minutes to wash it. Then, a running buffer (pH 5.5) was prepared that contains sodium alginate added to 100 mM malic acid and an arginine acid aqueous solution at a ratio of 0.8 wt %. This running buffer was passed through the capillary channel at the same pressure as described above, and thereby the B layer is formed on the A layer. With the capillary channel being filled with the running buffer, a sample containing hemoglobin dissolved in distilled water was injected into the capillary channel. Thereafter, a voltage of 10 kV was applied across both ends of the capillary channel, and thereby electrophoresis was carried out. The hemoglobin-containing sample was injected into the capillary channel from the anode side thereof. The hemoglobin that had been transferred was detected at an absorbance of 415 nm. This result is shown in the electropherogram in FIG. 3. As shown in FIG. 3, in this example, it was possible to detect normal hemoglobin (HbA0) and glycated hemoglobin (HbA1c) separately. Furthermore, as for the capillary channel used in this example, because the B layer was formed simply by passing through the running buffer therein after being washed, it was possible to carry out the analysis immediately.

Example 4

Figure 4:
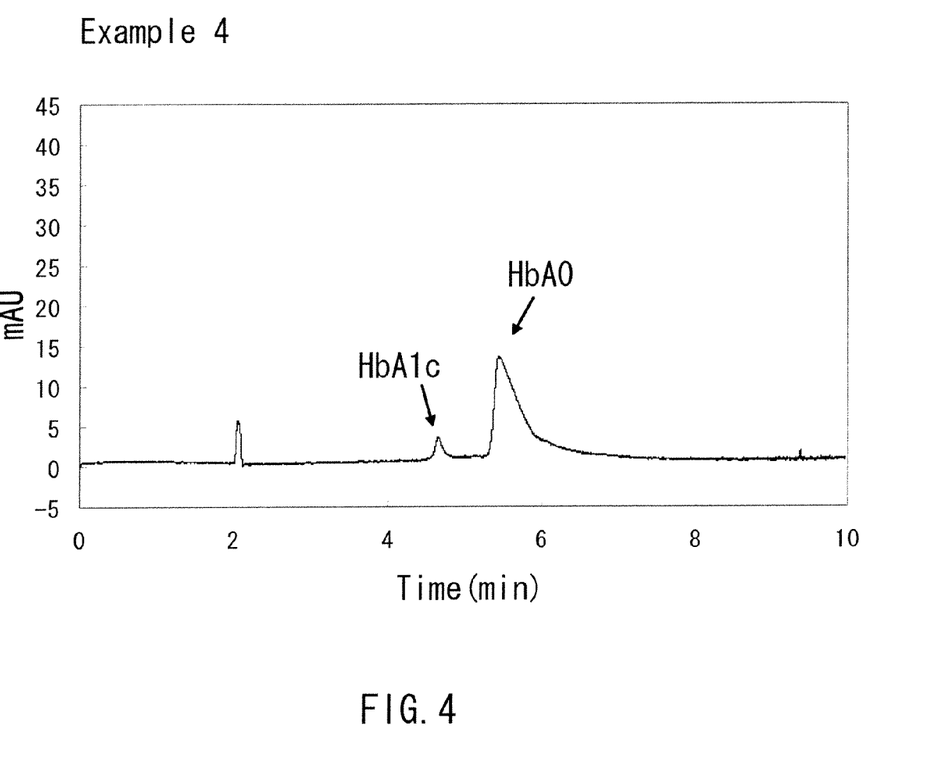
FIG. 4 is an electropherogram showing the result of analysis of hemoglobin in yet another example of the present invention.

A capillary channel (with an overall length of 32 cm, an effective length of 8.5 cm, and an inner diameter of 50 μm) made of fused silica was prepared. The capillary channel had an A layer formed with a silylation agent having an amino group that was fixed to the inner wall thereof by a covalent bond. Distilled water was passed through this capillary channel at a pressure of 0.1 MPa (1000 mbar) for 20 minutes to wash it. Then, a running buffer (pH 5.5) was prepared that contains heparin sodium added to 100 mM malic acid and an arginine acid aqueous solution at a ratio of 0.5 wt %. This running buffer was passed through the capillary channel at the same pressure as described above, and thereby the B layer was formed on the A layer. With the capillary channel being filled with the running buffer, a sample containing hemoglobin dissolved in distilled water was injected into the capillary channel. Thereafter, a voltage of 10 kV was applied across both ends of the capillary channel, and thereby electrophoresis was carried out. The hemoglobin-containing sample was injected into the capillary channel from the anode side thereof. The hemoglobin that had been transferred was detected at an absorbance of 415 nm. This result is shown in the electropherogram in FIG. 4. As shown in FIG. 4, in this example, it was possible to detect normal hemoglobin (HbA0) and glycated hemoglobin (HbA1c) separately. Furthermore, as for the capillary channel used in this example, because the B layer was formed simply by passing through the running buffer therein after being washed, it was possible to carry out the analysis immediately.

Example 5

Figure 5:
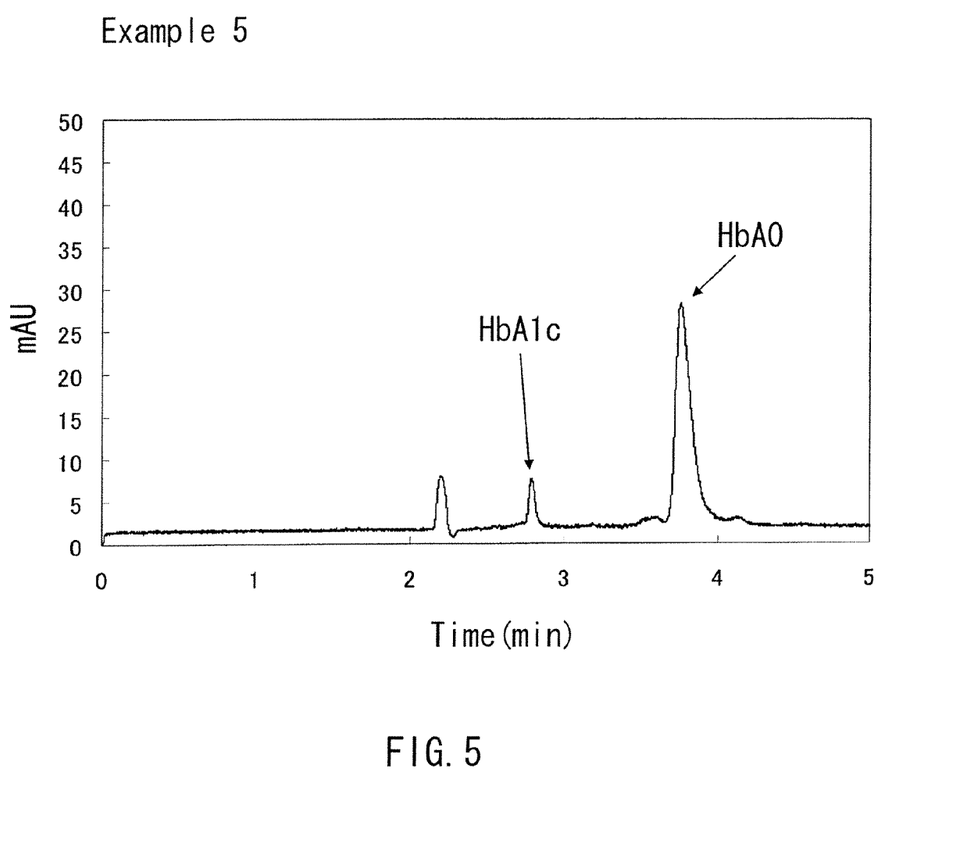
FIG. 5 is an electropherogram showing the result of analysis of hemoglobin in further another example of the present invention.

A capillary channel (with an overall length of 32 cm, an effective length of 8.5 cm, and an inner diameter of 50 μm) made of fused silica was prepared. The capillary channel had an A layer formed with poly(dimethylsiloxane) that was fixed to the inner wall thereof by a covalent bond. Distilled water was passed through this capillary channel at a pressure of 0.1 MPa (1000 mbar) for 20 minutes to wash it. Then, a running buffer (pH 5.5) was prepared that contains chondroitin sulfate added to 100 mM malic acid and an arginine acid aqueous solution at a ratio of 1.0 wt %. This running buffer was passed through the capillary channel at the same pressure as described above, and thereby the B layer was formed on the A layer. With the capillary channel being filled with the running buffer, a sample containing hemoglobin dissolved in distilled water was injected into the capillary channel. Thereafter, a voltage of 10 kV was applied across both ends of the capillary channel, and thereby electrophoresis was carried out. The hemoglobin-containing sample was injected into the capillary channel from the anode side thereof. The hemoglobin that had been transferred was detected at an absorbance of 415 nm. This result is shown in the electropherogram in FIG. 5. As shown in FIG. 5, in this example, it was possible to detect normal hemoglobin (HbA0) and glycated hemoglobin (HbA1c) separately. Furthermore, as for the capillary channel used in this example, because the B layer was formed simply by passing through the running buffer therein after being washed, it was possible to carry out the analysis immediately. In this state, the same analysis was carried out 10 times with the same sample as described above to evaluate repeatability. This result is shown in the following Table 2. In Table 2, as same as in Table 1, a relative area (%) denotes a ratio (%) of each peak area of the normal hemoglobin (HbA0) and the glycated hemoglobin (HbA1c) relative to a total peak area. As shown in Table 2, a value of coefficient of variation (CV) is small in each of the normal hemoglobin (HbA0) and the glycated hemoglobin (HbA1c). Thereby, it can be said that the analytical processes of the present invention is excellent in the precision.

TABLE 2

| No. | Relative Area (%) | |
|---|---|---|
| | HbA1c | HbA0 |
| 1 | 10.06 | 89.94 |
| 2 | 10.87 | 89.13 |
| 3 | 9.68 | 90.32 |
| 4 | 10.08 | 89.92 |
| 5 | 9.45 | 90.55 |
| 6 | 10.48 | 89.52 |
| 7 | 10.87 | 89.13 |
| 8 | 10.88 | 89.12 |
| 9 | 9.20 | 90.80 |
| 10 | 10.17 | 89.83 |
| Average | 10.17 | 89.83 |
| Coefficient of Variation(CV) | 5.9 | 0.7 |

INDUSTRIAL APPLICABILITY

As described above, according to the present invention, a sample such as hemoglobin can be analyzed easily with high precision by the capillary electrophoresis method. Moreover, since the present invention employs the capillary electrophoresis method, it also is possible to reduce the size of the analysis apparatus. The present invention is applicable to all the fields where a sample such as hemoglobin is to be analyzed, such as laboratory tests, biochemical examinations, and medical research. The intended use thereof is not limited and it is applicable to a wide range of fields.

The invention claimed is:

1. A process for analyzing glycated hemoglobin in a sample by a capillary electrophoresis method comprising:
    providing a sample comprising glycated hemoglobin,
    preparing a capillary channel for capillary electrophoresis, and
    performing electrophoretic separation of a chemical complex comprising the hemoglobin and a first anionic compound that is present in a running buffer solution at a pH in a range of 4.5 to 6 in the capillary channel,
    wherein the capillary channel comprises an inner wall coated with an A layer and a B layer that coats the A layer, wherein the A layer is covalently bonded to the inner wall and consists of a cationic compound, and the B layer consists of a second anionic compound which may be the same or different from the first anionic compound, and
    wherein the first anionic compound is an anionic polysaccharide.

2. The process of claim 1, wherein the B layer is formed by contacting the A layer with a solution containing the second anionic compound.

3. The process of claim 1, wherein the sample is introduced into the running buffer in the capillary channel, and wherein the electrophoretic separation is performed by applying voltage across both ends of the capillary channel.

4. The process of claim 1, wherein the second anionic compound is an anionic polysaccharide.

5. The process of claim 1, wherein the anionic polysaccharide is at least one selected from the group consisting of a sulfated polysaccharide, a carboxylated polysaccharide, a sulfonated polysaccharide, and a phosphorylated polysaccharide.

6. The process of claim 5, wherein the sulfated polysaccharide is chondroitin sulfate.

7. The process of claim 1, wherein the cationic compound is a silylation agent containing at least one of an amino group and an ammonium group.

8. The process of claim 7, wherein the silylation agent is selected from the group consisting of N-(2-diaminoethyl)-3-propyltrimethoxysilane, aminophenoxydimethylvinylsilane, 3-aminopropyldiisopropylethoxysilane, 3-aminopropylmethylbis(trimethylsiloxy)silane, 3-aminopropylpentamethyldisiloxane, 3-aminopropylsilanetriol, bis(P-aminophenoxy)dimethylsilane, 1,3-bis(3-aminopropyl)tetramethyldisiloxane, bis(dimethylamino)dimethylsilane, bis(dimethylamino)vinylmethylsilane, bis(2-hydroxyethyl)-3-aminopropyltriethoxysilane, 3-cyanopropyl(diisopropyl)dimethylaminosilane, (aminoethylaminomethyl)phenethyltrimethoxysilane, N-methylaminopropyltriethoxysilane, tetrakis(diethylamino)silane, tris(dimethylamino)chlorosilane and tris(dimethylamino)silane.

9. The process of claim 1, wherein the glycated hemoglobin is HbA1c.

10. The process of claim 1, wherein the first anionic compound is chondroitin sulfate.

11. The process of claim 1, wherein the second anionic compound is chondroitin sulfate.

* * * * *